US009044575B2

(12) United States Patent
Beasley et al.

(10) Patent No.: US 9,044,575 B2
(45) Date of Patent: Jun. 2, 2015

(54) CATHETERS WITH ENHANCED FLEXIBILITY AND ASSOCIATED DEVICES, SYSTEMS, AND METHODS

(71) Applicant: Medtronic Ardian Luxembourg S.a.r.l., Luxembourg (LU)

(72) Inventors: Rudy Beasley, Rohnert Park, CA (US); Justin Goshgarian, Santa Rosa, CA (US); Vincent Ku, Mountain View, CA (US)

(73) Assignee: Medtronic Adrian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/060,564

(22) Filed: Oct. 22, 2013

(65) Prior Publication Data
US 2014/0114287 A1    Apr. 24, 2014

Related U.S. Application Data

(60) Provisional application No. 61/717,067, filed on Oct. 22, 2012, provisional application No. 61/793,144, filed on Mar. 15, 2013, provisional application No. 61/800,195, filed on Mar. 15, 2013.

(51) Int. Cl.
*A61M 25/00* (2006.01)
*A61N 1/05* (2006.01)
(Continued)

(52) U.S. Cl.
CPC ....... *A61M 25/0054* (2013.01); *A61M 25/0053* (2013.01); *A61M 25/0051* (2013.01);
(Continued)

(58) Field of Classification Search
CPC ........... A61M 2025/09141; A61M 2205/0266; A61M 2025/0064; A61M 2025/09158; A61B 2017/00867; A61L 2400/16; A61L 31/022
USPC ................... 600/531, 585; 604/530, 525, 531
See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 0348136 | 12/1989 |
| EP | 0521595 | 1/1993 |

(Continued)

OTHER PUBLICATIONS

Allen, E.V., Sympathectomy for essential hypertension, Circulation, 1952, 6:131-140.

(Continued)

*Primary Examiner* — Nicholas Lucchesi
*Assistant Examiner* — Gerald Landry, II

(57) ABSTRACT

A neuromodulation catheter includes an elongate shaft and a neuromodulation element. The shaft includes two or more first cut shapes and two or more second cut shapes along a helical path extending around a longitudinal axis of the shaft. The first cut shapes are configured to at least partially resist deformation in response to longitudinal compression and tension on the shaft and torsion on the shaft in a first circumferential direction. The second cut shapes are configured to at least partially resist deformation in response to longitudinal compression on the shaft and torsion on the shaft in both first and second opposite circumferential directions.

13 Claims, 9 Drawing Sheets

(51) Int. Cl.
*A61N 1/06* (2006.01)
*A61B 18/14* (2006.01)
*A61B 18/00* (2006.01)

(52) U.S. Cl.
CPC  *A61N1/056* (2013.01); *A61N 1/06* (2013.01); *A61B 18/1492* (2013.01); *A61B 2018/00404* (2013.01); *A61B 2018/00434* (2013.01); *A61B 2018/00511* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,976,711 A | 12/1990 | Parins et al. |
| 4,998,923 A | 3/1991 | Samson et al. |
| 5,300,068 A | 4/1994 | Rosar et al. |
| 5,322,505 A | 6/1994 | Krause et al. |
| 5,358,514 A | 10/1994 | Schulman et al. |
| 5,368,591 A | 11/1994 | Lennox et al. |
| 5,399,164 A | 3/1995 | Snoke et al. |
| 5,423,744 A | 6/1995 | Gencheff et al. |
| 5,425,364 A | 6/1995 | Imran |
| 5,437,288 A | 8/1995 | Schwartz et al. |
| 5,477,856 A | 12/1995 | Lundquist |
| 5,484,400 A | 1/1996 | Edwards et al. |
| 5,558,643 A | 9/1996 | Samson et al. |
| 5,571,147 A | 11/1996 | Sluijter et al. |
| 5,599,319 A | 2/1997 | Stevens |
| 5,599,345 A | 2/1997 | Edwards et al. |
| 5,626,576 A | 5/1997 | Janssen |
| 5,672,174 A | 9/1997 | Gough et al. |
| 5,685,868 A | 11/1997 | Lundquist |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,865,787 A | 2/1999 | Shapland et al. |
| 5,871,444 A | 2/1999 | Ouchi |
| 5,891,110 A | 4/1999 | Larson et al. |
| 5,893,885 A | 4/1999 | Webster, Jr. |
| 5,916,178 A | 6/1999 | Noone et al. |
| 5,931,830 A | 8/1999 | Jacobsen et al. |
| 5,935,102 A | 8/1999 | Bowden et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,730 A | 2/2000 | Pagan |
| 6,048,338 A | 4/2000 | Larson et al. |
| 6,059,769 A | 5/2000 | Lunn et al. |
| 6,066,134 A | 5/2000 | Eggers et al. |
| 6,099,524 A | 8/2000 | Lipson et al. |
| 6,102,890 A | 8/2000 | Stivland et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,246,914 B1 | 6/2001 | de la Rama et al. |
| 6,251,092 B1 | 6/2001 | Qin et al. |
| 6,254,588 B1 | 7/2001 | Jones et al. |
| 6,273,876 B1 | 8/2001 | Klima et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,387,075 B1 | 5/2002 | Stivland et al. |
| 6,405,732 B1 | 6/2002 | Edwards et al. |
| 6,413,255 B1 | 7/2002 | Stern |
| 6,475,209 B1 | 11/2002 | Larson et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,562,034 B2 | 5/2003 | Edwards et al. |
| 6,585,718 B2 | 7/2003 | Hayzelden et al. |
| 6,611,720 B2 | 8/2003 | Hata et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,656,195 B2 | 12/2003 | Peters et al. |
| 6,669,670 B1 | 12/2003 | Muni et al. |
| 6,685,648 B2 | 2/2004 | Flaherty et al. |
| 6,716,207 B2 | 4/2004 | Farnholtz |
| 6,736,835 B2 | 5/2004 | Pellegrino et al. |
| 6,749,560 B1 | 6/2004 | Konstorum et al. |
| 6,845,267 B2 | 1/2005 | Harrison et al. |
| 6,850,801 B2 | 2/2005 | Kieval et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,058,456 B2 | 6/2006 | Pierce |
| 7,115,183 B2 | 10/2006 | Larson et al. |
| 7,119,183 B2 | 10/2006 | Seed et al. |
| 7,128,718 B2 | 10/2006 | Hojeibane et al. |
| 7,149,574 B2 | 12/2006 | Yun et al. |
| 7,162,303 B2 | 1/2007 | Levin et al. |
| 7,171,275 B2 | 1/2007 | Hata et al. |
| 7,221,979 B2 | 5/2007 | Zhou et al. |
| 7,276,062 B2 | 10/2007 | McDaniel et al. |
| 7,381,200 B2 | 6/2008 | Katoh et al. |
| 7,390,894 B2 | 6/2008 | Weinshilboum et al. |
| 7,402,151 B2 | 7/2008 | Rosenman et al. |
| 7,520,863 B2 | 4/2009 | Grewe et al. |
| 7,615,067 B2 | 11/2009 | Lee et al. |
| 7,617,005 B2 | 11/2009 | Demarais et al. |
| 7,637,903 B2 | 12/2009 | Lentz et al. |
| 7,647,115 B2 | 1/2010 | Levin et al. |
| 7,653,438 B2 | 1/2010 | Deem et al. |
| 7,682,319 B2 | 3/2010 | Martin et al. |
| 7,702,397 B2 | 4/2010 | Fredricks et al. |
| 7,708,704 B2 | 5/2010 | Mitelberg et al. |
| 7,717,948 B2 | 5/2010 | Demarais et al. |
| 7,727,187 B2 | 6/2010 | Lentz |
| 7,744,586 B2 | 6/2010 | Larson et al. |
| 7,744,856 B2 | 6/2010 | DeFilippi et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,780,646 B2 | 8/2010 | Farnholtz |
| 7,815,600 B2 | 10/2010 | Al-Marashi et al. |
| 7,815,637 B2 | 10/2010 | Ormsby et al. |
| 7,833,191 B2 | 11/2010 | Flach et al. |
| 7,914,467 B2 | 3/2011 | Layman et al. |
| 7,947,016 B2 | 5/2011 | Lentz |
| 7,989,042 B2 | 8/2011 | Obara et al. |
| 8,043,279 B2 | 10/2011 | Hisamatsu et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,376,865 B2 | 2/2013 | Forster et al. |
| 2002/0165532 A1 | 11/2002 | Hill et al. |
| 2002/0183682 A1 | 12/2002 | Darvish et al. |
| 2003/0050681 A1 | 3/2003 | Pianca et al. |
| 2003/0060858 A1 | 3/2003 | Kieval et al. |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0215186 A1 | 10/2004 | Cornelius et al. |
| 2005/0080400 A1 | 4/2005 | Corcoran et al. |
| 2005/0080409 A1 | 4/2005 | Young et al. |

(56) References Cited

U.S. PATENT DOCUMENTS

| | | | |
|---|---|---|---|
| 2005/0187579 A1 | 8/2005 | Danek et al. | |
| 2005/0228460 A1 | 10/2005 | Levin et al. | |
| 2005/0251094 A1* | 11/2005 | Peterson | 604/164.03 |
| 2005/0253680 A1* | 11/2005 | Mathews et al. | 337/395 |
| 2006/0004346 A1 | 1/2006 | Begg | |
| 2006/0064055 A1* | 3/2006 | Pile-Spellman et al. | 604/95.05 |
| 2006/0064123 A1 | 3/2006 | Bonnette et al. | |
| 2006/0095029 A1 | 5/2006 | Young et al. | |
| 2006/0100618 A1 | 5/2006 | Chan et al. | |
| 2006/0100687 A1 | 5/2006 | Fahey et al. | |
| 2006/0206150 A1 | 9/2006 | Demarais et al. | |
| 2006/0224112 A1 | 10/2006 | Lentz | |
| 2006/0271111 A1 | 11/2006 | Demarais et al. | |
| 2007/0005009 A1 | 1/2007 | Larson et al. | |
| 2007/0049999 A1* | 3/2007 | Esch et al. | 607/96 |
| 2007/0129720 A1 | 6/2007 | Demarais et al. | |
| 2007/0213687 A1 | 9/2007 | Barlow | |
| 2007/0265687 A1 | 11/2007 | Deem et al. | |
| 2007/0287955 A1 | 12/2007 | Layman et al. | |
| 2008/0077119 A1 | 3/2008 | Snyder et al. | |
| 2008/0097397 A1 | 4/2008 | Vrba | |
| 2008/0147001 A1 | 6/2008 | Al-Marashi et al. | |
| 2008/0287918 A1 | 11/2008 | Rosenman et al. | |
| 2008/0319418 A1 | 12/2008 | Chong | |
| 2008/0319513 A1 | 12/2008 | Pu et al. | |
| 2009/0036948 A1 | 2/2009 | Levin et al. | |
| 2009/0125001 A1 | 5/2009 | Anderson et al. | |
| 2009/0157048 A1 | 6/2009 | Sutermeister et al. | |
| 2009/0312606 A1 | 12/2009 | Dayton et al. | |
| 2010/0010526 A1 | 1/2010 | Mitusina | |
| 2010/0030217 A1 | 2/2010 | Mitusina | |
| 2010/0057037 A1 | 3/2010 | Webler | |
| 2010/0069882 A1 | 3/2010 | Jennings et al. | |
| 2010/0099952 A1 | 4/2010 | Adams | |
| 2010/0100073 A1 | 4/2010 | Lentz et al. | |
| 2010/0137860 A1 | 6/2010 | Demarais et al. | |
| 2010/0137952 A1 | 6/2010 | Demarais et al. | |
| 2010/0191112 A1 | 7/2010 | Demarais et al. | |
| 2010/0217184 A1 | 8/2010 | Koblish et al. | |
| 2010/0222851 A1 | 9/2010 | Deem et al. | |
| 2010/0222854 A1 | 9/2010 | Demarais et al. | |
| 2010/0228112 A1 | 9/2010 | Von Malmborg | |
| 2010/0305682 A1* | 12/2010 | Furst | 623/1.13 |
| 2010/0324482 A1 | 12/2010 | Farnholtz | |
| 2010/0331618 A1 | 12/2010 | Galperin | |
| 2010/0331776 A1 | 12/2010 | Salahieh et al. | |
| 2011/0034989 A1 | 2/2011 | Al-Marashi et al. | |
| 2011/0054464 A1 | 3/2011 | Werneth et al. | |
| 2011/0066105 A1 | 3/2011 | Hart et al. | |
| 2011/0245808 A1 | 10/2011 | Voeller et al. | |
| 2011/0276034 A1 | 11/2011 | Tomarelli et al. | |
| 2011/0288392 A1 | 11/2011 | De La Rama et al. | |
| 2012/0101413 A1 | 4/2012 | Beetel et al. | |
| 2012/0123328 A1* | 5/2012 | Williams | 604/95.05 |
| 2012/0130289 A1 | 5/2012 | Demarais et al. | |
| 2012/0130345 A1 | 5/2012 | Levin et al. | |
| 2012/0136350 A1* | 5/2012 | Goshgarian et al. | 606/41 |
| 2012/0143293 A1 | 6/2012 | Mauch et al. | |
| 2012/0172837 A1 | 7/2012 | Demarais et al. | |
| 2012/0204387 A1* | 8/2012 | Carlson et al. | 28/165 |
| 2012/0232529 A1* | 9/2012 | Buckley et al. | 604/531 |
| 2013/0006238 A1* | 1/2013 | Ditter et al. | 606/41 |
| 2014/0114288 A1 | 4/2014 | Beasley et al. | |
| 2014/0135736 A1* | 5/2014 | Hebert | 604/525 |
| 2014/0142509 A1* | 5/2014 | Bonutti et al. | 604/164.03 |

FOREIGN PATENT DOCUMENTS

| | | |
|---|---|---|
| EP | 0680355 | 11/1995 |
| EP | 0787019 | 8/1997 |
| EP | 0937481 | 8/1999 |
| EP | 0951244 | 10/1999 |
| EP | 1334743 | 8/2003 |
| EP | 1656963 | 5/2006 |
| EP | 1839697 | 10/2007 |
| EP | 1982741 | 10/2008 |
| EP | 2106821 | 10/2009 |
| EP | 2332607 | 6/2011 |
| EP | 2351593 | 8/2011 |
| EP | 2398540 | 12/2011 |
| WO | WO-9525472 | 9/1995 |
| WO | WO9703611 | 2/1997 |
| WO | WO-9736548 | 10/1997 |
| WO | WO-99/00060 | 1/1999 |
| WO | WO-9911313 | 3/1999 |
| WO | WO-0122897 | 4/2001 |
| WO | WO-0170114 | 9/2001 |
| WO | WO-2005041748 | 5/2005 |
| WO | WO-2005110528 | 11/2005 |
| WO | WO-2006041881 | 4/2006 |
| WO | WO-2007008954 | 1/2007 |
| WO | WO-2009108997 | 9/2009 |
| WO | WO-2009125575 | 10/2009 |
| WO | WO-2014066432 | 5/2014 |
| WO | WO-2014066439 | 5/2014 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney-Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of-Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009.

Schlaich, M.P. et al., "Renal Denervation as a Therapeutic Approach for Hypertension: Novel Implictions for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

(56) References Cited

OTHER PUBLICATIONS

Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
European Search Report for European Application No. 13159256, Date Mailed: Oct. 17, 2013, 6 pages.
International Search Report and Written Opinion for International Application No. PCT/US2013/066248, Mailed Apr. 14, 2014, 28 pages.
International Search Report and Written Opinion for International Application No. PCT/US2013/066256, Mailed Apr. 14, 2014, 28 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n. l.), 4 pages.
"Renal Denervation Technology of Vessix Vascular, Inc. been acquired by Boston Scientific Corporation (BSX) to pay up to $425

(56) References Cited

OTHER PUBLICATIONS

Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).

(56) References Cited

OTHER PUBLICATIONS

Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.

* cited by examiner

CATHETERS WITH ENHANCED FLEXIBILITY AND ASSOCIATED DEVICES, SYSTEMS, AND METHODS

CROSS-REFERENCE TO RELATED APPLICATIONS

This application claims the benefit of the following applications:
(a) U.S. Provisional Application No. 61/717,067, filed Oct. 22, 2012;
(b) U.S. Provisional Application No. 61/793,144, filed Mar. 15, 2013; and
(c) U.S. Provisional Application No. 61/800,195, filed Mar. 15, 2013.

The foregoing applications are incorporated herein by reference in their entireties.

TECHNICAL FIELD

The present technology is related to catheters. In particular, at least some embodiments are related to neuromodulation catheters having one or more cuts and/or other features that enhance flexibility, such as to facilitate intravascular delivery via transradial or other suitable percutaneous transluminal approaches.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
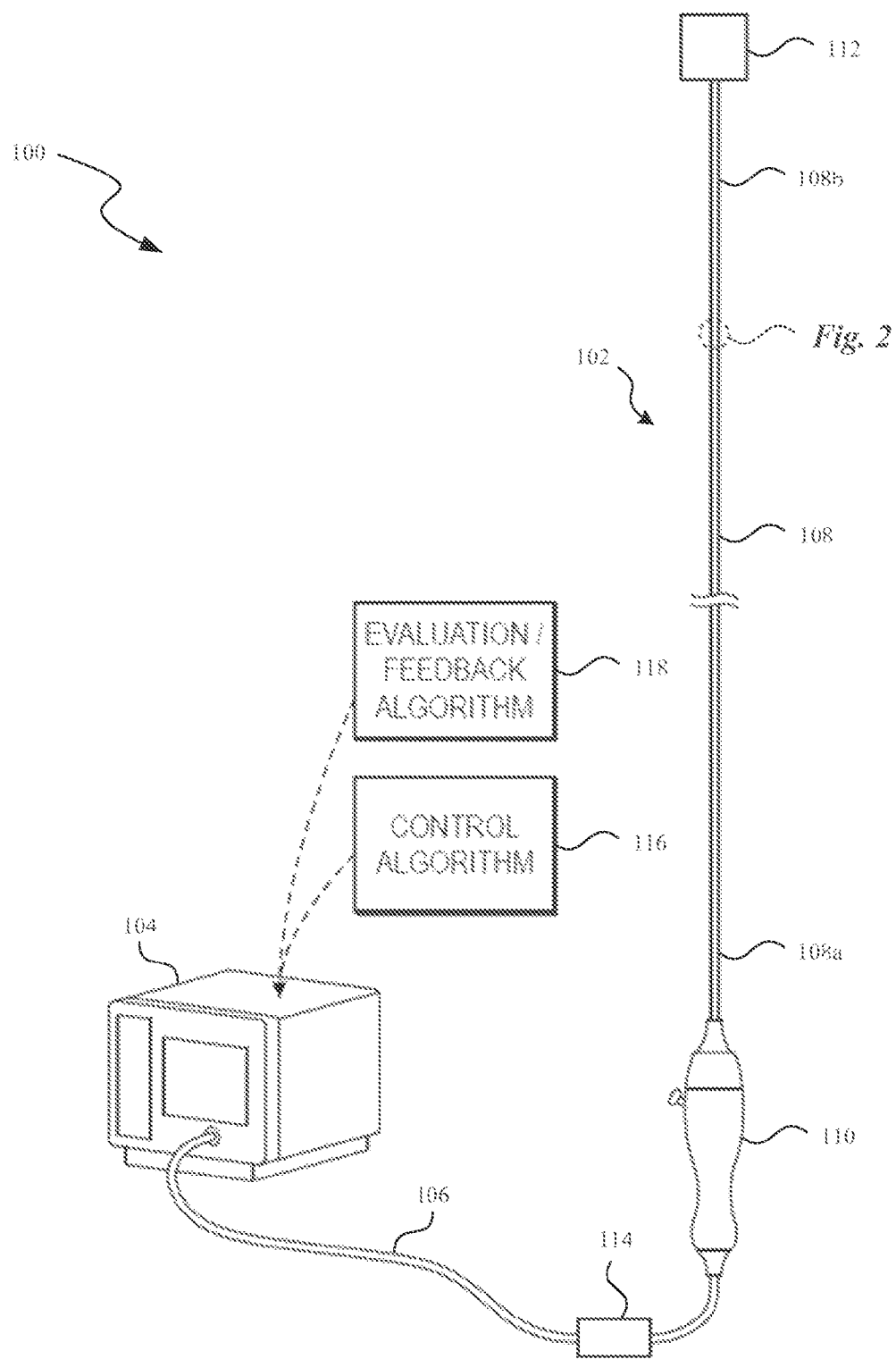
FIG. 1 is a partially schematic perspective view illustrating a therapeutic system including a neuromodulation catheter configured in accordance with an embodiment of the present technology.

Neuromodulation catheters configured in accordance with at least some embodiments of the present technology include elongate shafts having one or more cuts and/or other features that enhance flexibility without unduly compromising desirable axial stiffness (e.g., pushability or other responsiveness to axial force) and/or desirable torsional stiffness (e.g., torqueability or other responsiveness to torsional force). For example, a neuromodulation catheter configured in accordance with a particular embodiment of the present technology is sufficiently flexible in some respects to facilitate deployment via a relatively long and/or tortuous intravascular path without excessive resistance, while still being sufficiently stiff in other respects so as to allow intravascular navigation or other suitable manipulation via an extracorporeal handle. Desirable axial stiffness can include, for example, the capability of the shaft to be advanced or withdrawn along the length of an intravascular path without significantly buckling or elongating. Desirable torsional stiffness can include, for example, the capability of the shaft to distally transfer rotational motion (e.g., from a handle at a proximal end portion of the shaft to a neuromodulation element operably connected to the shaft via a distal end portion of the shaft) with close correspondence (e.g., at least about one-to-one correspondence). In addition or alternatively, desirable torsional stiffness can include the capability of the shaft to distally transfer rotational motion without causing whipping and/or diametrical deformation of the shaft. Desirable axial and torsional stiffness together can facilitate predictable and controlled transmission of axial and torsional force from the proximal end portion of the shaft toward the distal end portion of the shaft while a neuromodulation catheter is in use.

Metal hypodermic (needle) tubing, aka hypotubing, is commonly incorporated into small-diameter shafts of medical catheters to utilize the wire-like physical properties of such material along with the useable lumen extending therethrough. However, solid-walled metal tubing also has known limitations regarding flexibility and kink resistance, and various designs have utilized slits, slots or other openings in the tubing wall to achieve improvements in flexibility. Such modifications to the wall structure have always brought about compromises in physical properties in tension, compression, and torsion. Thus, in at least some conventional neuromodulation catheters, imparting flexibility can require unduly sacrificing axial stiffness and/or torsional stiffness. For example, creating a continuous helical cut in a relatively rigid hypotube of a shaft tends to increase the flexibility of the shaft, but, in some instances, the resulting coils between turns of the cut may also tend to separate to an undesirable degree in response to tension on the shaft and/or torsion on the shaft in at least one circumferential direction. In some cases, this separation can cause a permanent or temporary change in the length of the shaft (e.g., undesirable elongation of the shaft), a permanent or temporary diametrical deformation of the shaft (e.g., undesirable flattening of a cross-section of the shaft), and/or torsional whipping. Such shaft behavior can interfere with intravascular navigation and/or have other undesirable effects on neuromodulation procedures.

Due, at least in part, to enhanced flexibility in combination with desirable axial and torsional stiffness, neuromodulation catheters configured in accordance with at least some embodiments of the present technology can be well-suited for intravascular delivery to treatment locations (e.g., treatment locations within or otherwise proximate to a renal artery of a human patient) via transradial approaches (e.g., approaches that include the radial artery, the subclavian artery, and the descending aorta). Transradial approaches are typically more tortuous and longer than femoral approaches and at least some other commonly used approaches. Transradial approaches can be desirable for accessing certain anatomy, but other types of approaches (e.g., femoral approaches) may be desirable in particularly tortuous anatomy or vessels having relatively small diameters. In some instances, however, use of transradial approaches can provide certain advantages over use of femoral approaches. In some cases, for example, use of transradial approaches can be associated with increased patient comfort, decreased bleeding, and/or faster sealing of the percutaneous puncture site relative to use of femoral approaches.

In addition to or instead of facilitating intravascular delivery via transradial approaches, neuromodulation catheters configured in accordance with at least some embodiments of the present technology can be well suited for intravascular delivery via one or more other suitable approaches, such as other suitable approaches that are shorter or longer than transradial approaches and other suitable approaches that are less tortuous or more tortuous than transradial approaches. For example, neuromodulation catheters configured in accordance with at least some embodiments of the present technology can be well suited for intravascular delivery via brachial approaches and/or femoral approaches. Even when used with approaches that are generally shorter and/or less tortuous than transradial approaches, the combination of flexibility and desirable axial and torsional stiffness associated with neuromodulation catheters configured in accordance with at least some embodiments of the present technology can be beneficial, such as to accommodate anatomical differences between patients and/or to reduce vessel trauma during delivery, among other potential benefits.

Specific details of several embodiments of the present technology are described herein with reference to FIGS. 1-17. Although many of the embodiments are described herein with respect to devices, systems, and methods for intravascular renal neuromodulation, other applications and other embodiments in addition to those described herein are within the scope of the present technology. For example, at least some embodiments may be useful for intraluminal neuromodulation, for extravascular neuromodulation, for non-renal neuromodulation, and/or for use in therapies other than neuromodulation. It should be noted that other embodiments in addition to those disclosed herein are within the scope of the present technology. For example, in still other embodiments, the technology described herein may be used in devices, systems and methods for stent delivery and balloon angioplasty. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selected Examples of Neuromodulation Catheters and Related Devices

FIG. 1 is a partially schematic perspective view illustrating a therapeutic system 100 configured in accordance with an embodiment of the present technology. The system 100 can include a neuromodulation catheter 102, a console 104, and a cable 106 extending therebetween. The neuromodulation catheter 102 can include an elongate shaft 108 having a proximal end portion 108a and a distal end portion 108b. A handle 110 of the neuromodulation catheter 102 can be operably connected to the shaft 108 via the proximal end portion 108a, and a neuromodulation element 112 of the neuromodulation catheter 102 can be operably connected to the shaft 108 via the distal end portion 108b. The shaft 108 can be configured to locate the neuromodulation element 112 intravascularly at a treatment location within or otherwise proximate to a body lumen (e.g., a blood vessel, a duct, an airway, or another naturally occurring lumen within the human body), and the neuromodulation element 112 can be configured to provide or support a neuromodulation treatment at the treatment location. The shaft 108 and the neuromodulation element 112 can be 2, 3, 4, 5, 6, or 7 French or one or more other suitable sizes.

In some embodiments, intravascular delivery of the neuromodulation catheter 102 includes percutaneously inserting a guide wire (not shown) into a body lumen of a patient and moving the shaft 108 and the neuromodulation element 112 along the guide wire until the neuromodulation element 112 reaches a suitable treatment location. In other embodiments, the neuromodulation catheter 102 can be a steerable or non-steerable device configured for use without a guide wire. In still other embodiments, the neuromodulation catheter 102 can be configured for delivery via a guide catheter or sheath (not shown).

The console 104 can be configured to control, monitor, supply, and/or otherwise support operation of the neuromodulation catheter 102. Alternatively, the neuromodulation catheter 102 can be self-contained or otherwise configured for operation without connection to the console 104. When present, the console 104 can be configured to generate a selected form and/or magnitude of energy for delivery to tissue at the treatment location via the neuromodulation element 112 (e.g., via one or more energy delivery elements (not shown) of the neuromodulation element 112). The console 104 can have different configurations depending on the treatment modality of the neuromodulation catheter 102. When the neuromodulation catheter 102 is configured for electrode-based, heat-element-based, or transducer-based treatment, for example, the console 104 can include an energy generator (not shown) configured to generate radio frequency (RF) energy (e.g., monopolar and/or bipolar RF energy), pulsed energy, microwave energy, optical energy, ultrasound energy (e.g., intravascularly delivered ultrasound, extracorporeal ultrasound, and/or high-intensity focused ultrasound (HIFU)), cryotherapeutic energy, direct heat energy, chemicals (e.g., drugs and/or other agents), radiation (e.g., infrared, visible, and/or gamma radiation), and/or another suitable type of energy. When the neuromodulation catheter 102 is configured for cryotherapeutic treatment, for example, the console 104 can include a refrigerant reservoir (not shown) and can be configured to supply the neuromodulation catheter 102 with refrigerant. Similarly, when the neuromodulation catheter 102 is configured for chemical-based treatment (e.g., drug infusion), the console 104 can include a chemical reservoir (not shown) and can be configured to supply the neuromodulation catheter 102 with one or more chemicals.

In some embodiments, the system 100 includes a control device 114 along the cable 106. The control device 114 can be configured to initiate, terminate, and/or adjust operation of one or more components of the neuromodulation catheter 102 directly and/or via the console 104. In other embodiments, the control device 114 can be absent or have another suitable location (e.g., within the handle 110). The console 104 can be configured to execute an automated control algorithm 116 and/or to receive control instructions from an operator. Furthermore, the console 104 can be configured to provide feedback to an operator before, during, and/or after a treatment procedure via an evaluation/feedback algorithm 118.

Figure 2:
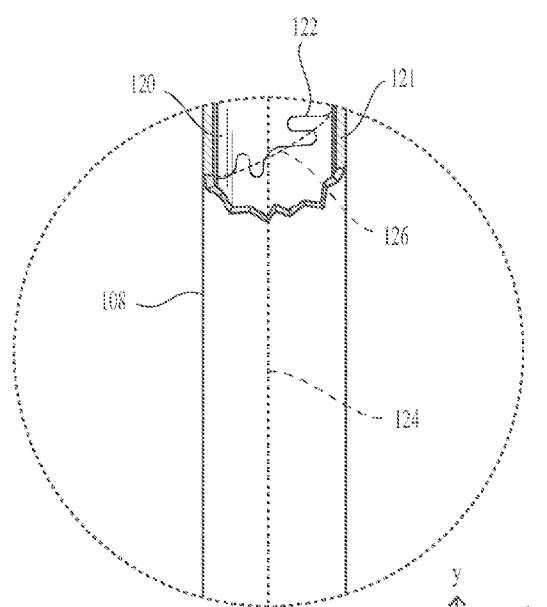
FIG. 2 is an enlarged partially cut-away side view of a shaft of the neuromodulation catheter shown in FIG. 1 illustrating a hypotube of the shaft and a cut extending along a helical path having varying pitch along the length of the shaft.

FIG. 2 is an enlarged partially cut-away side view of the shaft 108 illustrating a hypotube 120 concentrically disposed within an outside wall 121. The hypotube 120 can be configured to reinforce the shaft 108 against collapsing from lateral compression. For example, the hypotube 120 can be made of a relatively strong material (e.g., nitinol, stainless steel, or another suitable metal). The hypotube 120 may be disposed within all or a portion of the shaft 108. In some embodiments, for example, the hypotube 120 may only be disposed at a distal section of the shaft 108, and a proximal section of the shaft 108 may have a different arrangement and/or configuration. Tubes made of relatively strong materials tend to be relatively stiff (e.g., resistant to bending) when unmodified. To increase the flexibility of the neuromodulation catheter 102, the shaft 108 can include a cut 122 extending at least partially through a wall thickness of the hypotube 120, the outside wall 121, or another suitable portion of the shaft 108. For example, the shaft 108 can have a longitudinal axis 124 and the cut 122 can follow a helical path 126 that extends about the longitudinal axis 124 (e.g., a coiled, spiral, or other similar form having two or more turns consistently or variably spaced along the longitudinal axis 124). The cut 122 can be continuous or discontinuous along the helical path 126. Furthermore, the shaft 108 can be cut along more than one helical path 126 (e.g., a double helix having two or more helical paths 126 having the same "hand" or chirality and spaced apart along the longitudinal axis 124). The cut 122 can be formed, for example, using laser etching, electrical discharge machining, chemical etching, or other suitable techniques.

Figure 3:
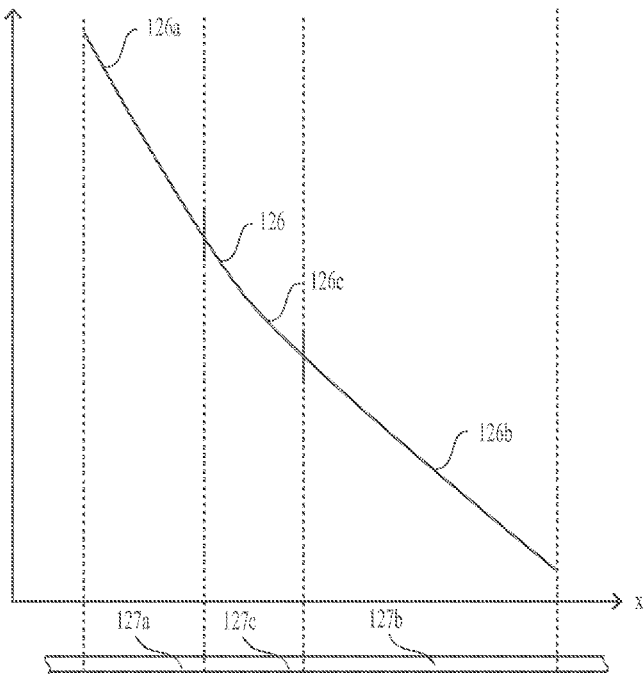
FIG. 3 is a two-dimensional representation of the helical path shown in FIG. 2 and a portion of the shaft shown in FIG. 1.

FIG. 3 is a two-dimensional representation of the helical path 126. In particular, FIG. 3 is a representation of the helical path 126 and a portion of the shaft 108 with the x-axis in FIG. 3 corresponding to the longitudinal axis 124 along at least a portion of the length of the shaft 108 and the y-axis in FIG. 3 corresponding to the circumference of the shaft 108. In other words, FIG. 3 illustrates the helical path 126 as though at least a portion of the shaft 108 were aligned with the x-axis and rolled along the y-axis with the helical path 126 unwinding to a flat ribbon or making an imprinted image as the shaft 108 is rolled. The helical path 126 can include a first portion 126a, a second portion 126b, and a third portion 126c therebetween. The first portion 126a, the second portion 126b, and the third portion 126c can extend around portions of the longitudinal axis 124 corresponding to a first segment 127a, a second segment 127b, and a third segment 127c of the shaft 108, respectively. In some embodiments, the first segment 127a is distal to the second and third segments 127b, 127c, and the third segment 127c is between the first and second segments 127a, 127b. In other embodiments, the first, second, and third segments 127a-c can be reversed or have another suitable arrangement. The first, second, and third segments 127a-c can be directly adjacent to one another or spaced apart from one another along the longitudinal axis 124. Furthermore, the first segment 127a can be directly adjacent to or spaced apart from a distalmost portion of the shaft 108 (e.g., a junction between the shaft 108 and the neuromodulation element 112), and the second segment 127b can be directly adjacent to or spaced apart from a proximalmost portion of the shaft 108 (e.g., a junction between the shaft 108 and the handle 110).

As shown in FIG. 3, the first, second, and third portions 126a-126c of the helical path 126 can have different slopes when transposed two-dimensionally. These slopes can correspond to the axial density (e.g., frequency or pitch angle) of turns, shapes, or other suitable features of the cut 122 along the longitudinal axis 124. For example, the first portion 126a of the helical path 126 can have a greater slope than the second portion 126b, and the third portion 126c can be curved with a slope that gradually transitions between the slopes of the first and second portions 126a, 126b. Accordingly, the cut 122 can have a greater axial density of turns, shapes, or other suitable features along a portion of the longitudinal axis 124 corresponding to the first segment 127a than along a portion of the longitudinal axis 124 corresponding to the second segment 127b. Similarly, the axial density of turns, shapes, or other suitable features of the cut 122 along the longitudinal axis 124 can increase gradually or in another suitable manner along the third segment 127c from the second segment 127b toward the first segment 127a. For example, gradually increasing or otherwise transitioning the axial density of turns, shapes, slope, type, size/dimension, or other suitable features of the cut 122 may reduce focused stress on the shaft 108, which can reduce or eliminate kinking or other undesirable behavior of the shaft 108 when it bends.

By varying the axial density of turns, shapes, or other suitable features of the cut 122, different segments of the shaft 108 can have different levels of flexibility. For example, with reference to FIGS. 1-3 together, a greater axial density of turns, shapes, or other suitable features can correspond to greater flexibility than a lesser axial density of turns, shapes, or other suitable features. In some cases, a distance along the longitudinal axis 124 between the neuromodulation element 112 and a cut segment of the shaft 108 (e.g., the first, second, or third segment 127a-c) can be selected such that the cut segment tends to be disposed in or near a particular anatomical location when the neuromodulation catheter 102 is in use. For example, the distance along the longitudinal axis 124 between the neuromodulation element 112 and the cut segment can be selected such that the cut segment tends to be at least proximate to a relatively sharply angled or otherwise relatively tortuous anatomic region of an approach (e.g., a transradial or other suitable approach) when the neuromodulation element 112 is at a selected treatment location (e.g., a treatment location within or otherwise proximate to a renal artery of a human patient). The relatively sharply angled or otherwise relatively tortuous region, for example, can be a region within or otherwise proximate to a subclavian artery (e.g., a portion of a subclavian artery adjacent to the descending aorta), an ostium of a renal artery, or another suitable anatomical feature. The axial density of turns, shapes, or other suitable features of the cut 122 along different segments of the shaft 108 and the relative flexibilities of the different segments can be selected to facilitate transradial catheterization or deployment of the neuromodulation catheter 102 via another suitable approach. In some embodiments, an axial density of turns, shapes, or other suitable features of the cut 122 along the longitudinal axis 124 varies along the length of the shaft 108 (e.g., to tailor the shaft 108 to the tortuosity or other geometry of different portions of a transradial or other suitable approach). In other embodiments, the axial density of turns, shapes, or other suitable features of the cut 122 along the longitudinal axis 124 can be consistent along the length of the shaft 108 (e.g., to increase the overall flexibility of the shaft 108).

Figure 4:
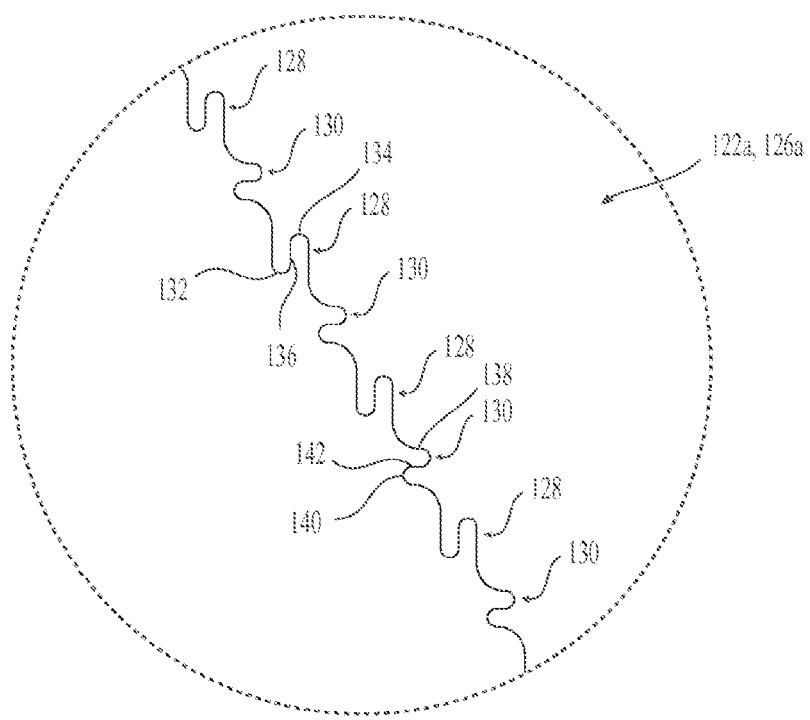
FIG. 4 is a two-dimensional representation of the cut shown in FIG. 2 along a first portion of the helical path shown in FIG. 3.

FIG. 4 is a two-dimensional representation of the cut 122 along the first portion 126a of the helical path 126. Such a two-dimensional representation is as if the shaft were rolled over a flat surface to leave an imprint of the cut shape therein. In some instances, these two dimensional representations can be used as input for an automated manufacturing process used to form cut shapes along a path in a tubular workpiece. With reference to FIGS. 2-4 together, the shaft 108 can include two or more first cut shapes 128 and two or more second cut shapes 130 interspersed along the helical path 126, with the first and second cut shapes 128, 130 forming portions of the cut 122. The first cut shapes 128 can be configured to at least partially interlock to thereby resist deformation in response to a set of three types of force acting on the shaft 108, and the second cut shapes 130 can be configured to at least partially interlock to thereby resist deformation in response to a different, complementary set of three types of force acting on the shaft 108. The sets can be different combinations of (a) compression along the longitudinal axis 124, (b) tension along the longitudinal axis 124, (c) torsion in a first circumferential direction perpendicular to the longitudinal axis 124, and (d) torsion in a second, opposite circumferential direction perpendicular to the longitudinal axis 124. For example, the first cut shapes 128 can be configured to at least partially resist deformation in response to compression on the shaft 108, tension on the shaft 108, and torsion on the shaft 108 in the first circumferential direction, and the second cut shapes 130 can be configured to at least partially resist deformation in response to compression on the shaft 108, torsion on the shaft 108 in the first circumferential direction, and torsion on the shaft 108 in a second circumferential direction opposite to the first circumferential direction. The first cut shapes 128 can be less resistant to deformation in response to torsion on the shaft 108 in the second circumferential direction than the second cut shapes 130. Similarly, the second cut shapes 130 can be less resistant to deformation in response to tension on the shaft 108 than the first cut shapes 128. Working together, the first and second cut shapes 128, 130 can provide the shaft 108 with sufficient resistance to deformation in response to all types of axial and torsional force that may act on the shaft 108 during use of the neuromodulation catheter 102.

In some embodiments, the first and second cut shapes 128, 130 are sinusoidal and have amplitudes with different (e.g., perpendicular) orientations relative to the longitudinal axis 124. In other embodiments, the first and second cut shapes 128, 130 can have other suitable forms. For example, as shown in FIG. 4, the first cut shapes 128 can individually include a first peak 132 (e.g., a first finger) and a second peak 134 (e.g., a second finger) with a first interface 136 therebetween. The first interface 136 can be perpendicular to the longitudinal axis 124 (FIG. 2). The second cut shapes 130 can individually include a third peak 138 (e.g., a third finger) and a fourth peak 140 (e.g., a fourth finger) with a second interface 142 therebetween. The second interface 142 can be parallel to the longitudinal axis 124. Alternatively, the first and second interfaces 136, 142 can have other suitable angles relative to the longitudinal axis 124, such as other suitable angles in which an angle between the first interface 136 and the longitudinal axis 124 is greater than an angle between the second interface 142 and the longitudinal axis 124. The first and second cut shapes 128, 130 can be configured to at least partially resist deformation in response to forces perpendicular to the first and second interfaces 136, 142, respectively. For example, such forces can cause the first and second peaks 132, 134 or the third and fourth peaks 138, 140 to at least partially interlock and thereby prevent or reduce widening of the cut 122.

Figure 5:
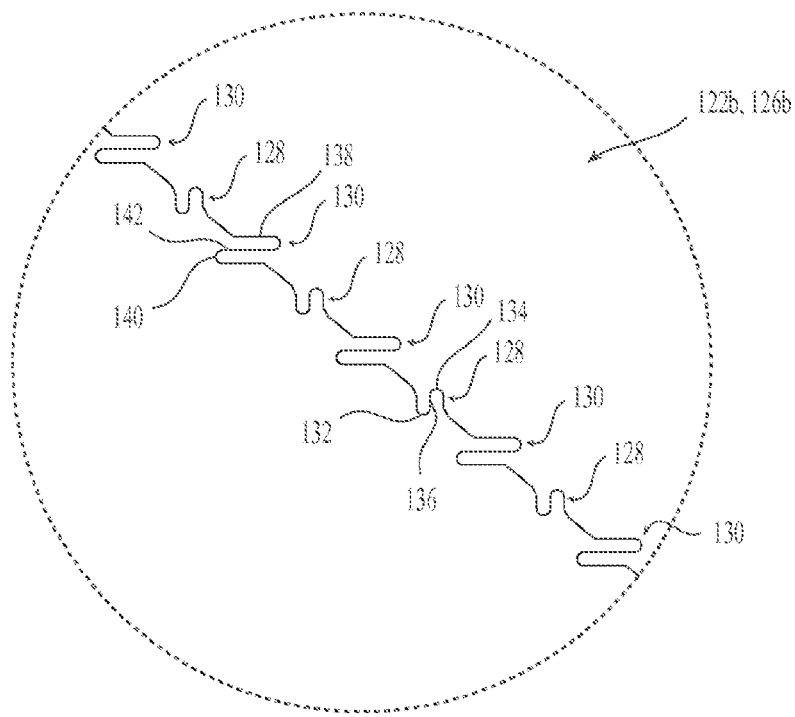
FIG. 5 is a two-dimensional representation of the cut shown in FIG. 2 along a second portion of the helical path shown in FIG. 3.

FIG. 5 is a two-dimensional representation of the cut 122 along the second portion 126b of the helical path 126. With reference to FIGS. 2, 3 and 5 together, an average length of the first interfaces 136, an average length of the second interfaces 142, or both can be different at different portions of the helical path 126. For example, the average length of the second interfaces 142 can be greater among the second cut shapes 130 along the second portion 126b of the helical path 126 and the second segment 127b of the shaft 108 than among the second cut shapes 130 along the first portion 126a of the helical path 126 and the first segment 127a of the shaft 108. In some cases, the average length of the first interfaces 136, the second interfaces 142, or both are selected based on different axial densities of turns, shapes, or other suitable features of the cut 122 at different segments of the shaft 108. For example, when the axial density is greater, the lengths of the first and second interfaces 136, 142 can be more restricted than when the axial density is lower (e.g., so as to avoid overlapping at adjacent turns).

Figure 6:
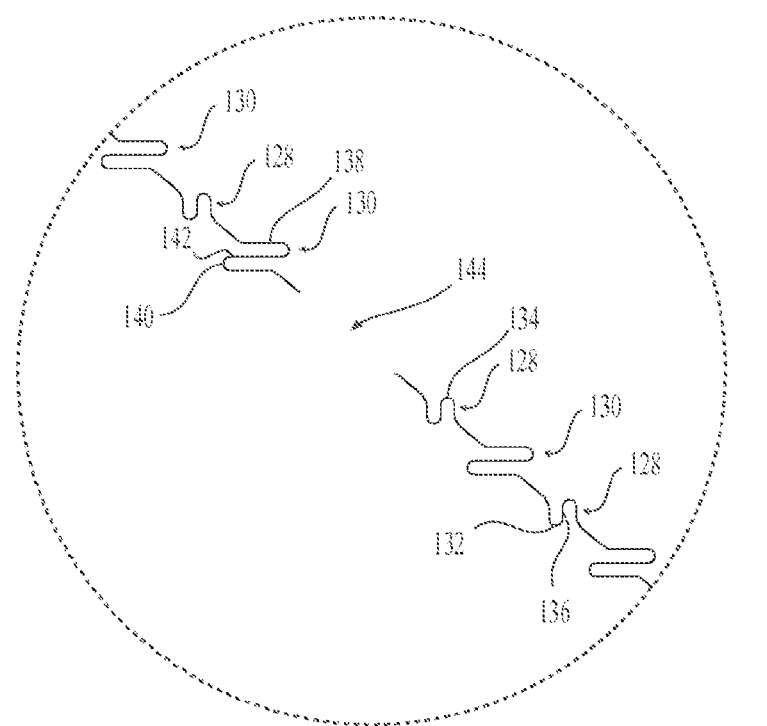
FIGS. 6-9B are two-dimensional representations of cuts along portions of helical paths configured in accordance with embodiments of the present technology.
Figure 7:
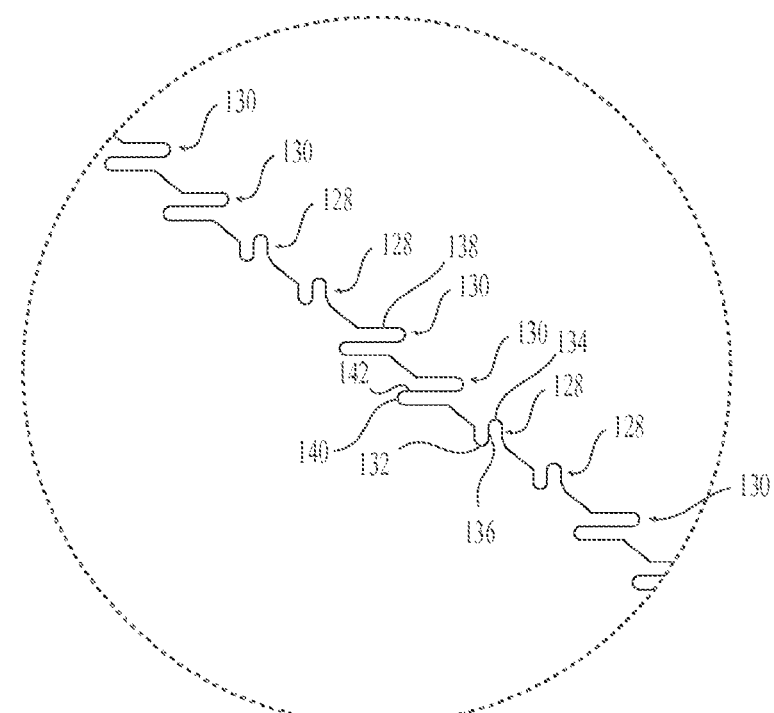

FIGS. 6-9B are two-dimensional representations of cuts along portions of helical paths configured in accordance with further embodiments of the present technology. As shown in FIG. 6, for example, in some embodiments a shaft 108 includes an uncut region 144 with the first and second cut shapes 128, 130 positioned along portions of a helical path on either side of the uncut region 144. For example, the uncut region 144 can be one of many uncut regions 144 interspersed among the first and second cut shapes 128, 130 along the helical path. In other embodiments, the first and second cut shapes 128, 130 can be portions of a continuous cut. For example, as shown in FIG. 7, the first and second cut shapes 128, 130 can be in suitable patterns along the helical path other than one-to-one alternating patterns. Suitable patterns can include, for example, random patterns, non-random patterns, two-to-one alternating patterns, two-to-two alternating patterns, and three-to-two alternating patterns, among others. Furthermore, the spacing between adjacent first and second cut shapes 128, 130 can be consistent or variable.

Figure 8:
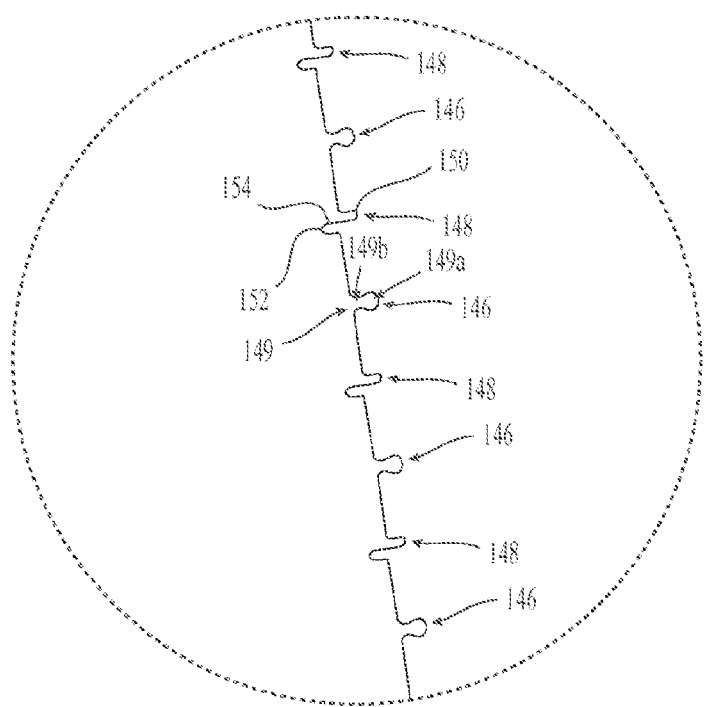

Referring next to FIG. 8, a shaft can include two or more third cut shapes 146 and two or more fourth cut shapes 148 interspersed along a helical path. The individual third cut shapes 146 can be configured to fully interlock rather than partially interlock. For example, the individual third cut shapes 146 can be configured to at least partially resist deformation in response to compression on the shaft, tension on the shaft, torsion on the shaft in the first circumferential direction, and torsion on the shaft in the second circumferential direction. The shaft, for example, can include tabs 149 (e.g., protrusions, lobes, or other suitable structures) adjacent to the third cut shapes 146, with the third cut shapes 146 forming recesses complementary to the tabs 149. The individual tabs 149 can include a flared portion 149a (e.g., a rounded head portion) and a restricted portion 149b (e.g., a rounded neck portion), or other suitable structures. The fourth cut shapes 148 can be sinusoidal and have amplitudes oriented perpendicularly to the helical path. For example, the individual fourth cut shapes 148 can include a first peak 150 and a second peak 152 with an interface 154 therebetween that is diagonal relative to a longitudinal axis of the shaft and perpendicular to the helical path.

Figure 9A:
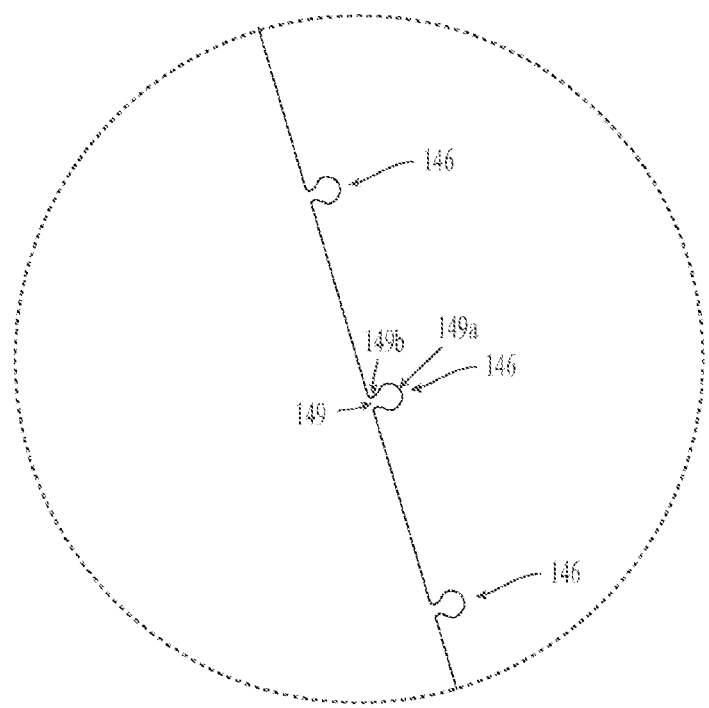
Figure 9B:
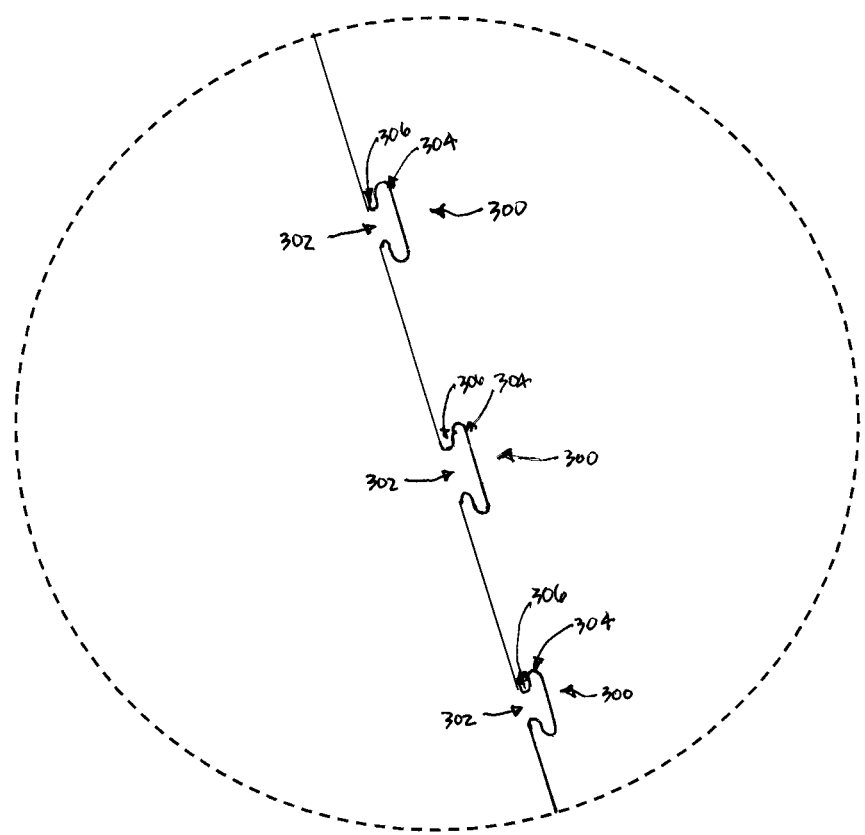

As shown in FIGS. 9A and 9B, in some embodiments a shaft includes the third cut shapes 146 without the fourth cut shapes 148. Referring to FIG. 9B, for example, the shaft includes tabs 302 adjacent to respective third cut shapes 300. The individual tabs 302 and corresponding third cut shapes 300, for example, can comprise a wedge-shaped arrangement with the tabs 302 including a wedge-shaped portion 304 (i.e., a "tail") and a restricted neck portion 306, while the complementary third cut shapes 300 form recesses or sockets (i.e., "tail sockets") complementary to the tabs 302. In some embodiments, the tabs 302 and third cut shapes 300 may fit snugly with very little room between the respective portions of the two components. In other embodiments, however, there may be some space between at least a portion of each wedge-shaped portion 304 and the complementary socket portion to allow some amount of relative movement between the components.

In other embodiments, the shaft can include the fourth cut shapes 148 without the third cut shapes 146. Although the third and fourth cut shapes 146, 148 are potentially useful alone or in combination with other cut shapes, it is expected that combinations of the first and second cut shapes 128, 130 may be more stable than the third and fourth cut shapes 146, 148 alone or in combination during use of a neuromodulation catheter. For example, is it expected that combinations of cut shapes that impart resistance to complementary sets of fewer than all types of axial and torsional force that may act on a shaft during use of a neuromodulation catheter may facilitate dissipation of localized stresses along a cut. It will further be appreciated that catheters configured in accordance with embodiments of the present technology can include various combinations of cut shapes tailored to provide a desired level of flexibility and/or control for different applications.

Figure 10:
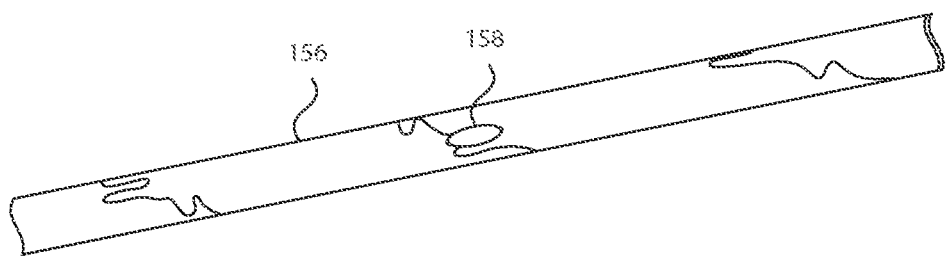
FIGS. 10-12 are perspective views of shaft segments having guide wire exit openings with different positions relative to cuts configured in accordance with embodiments of the present technology.
Figure 11:
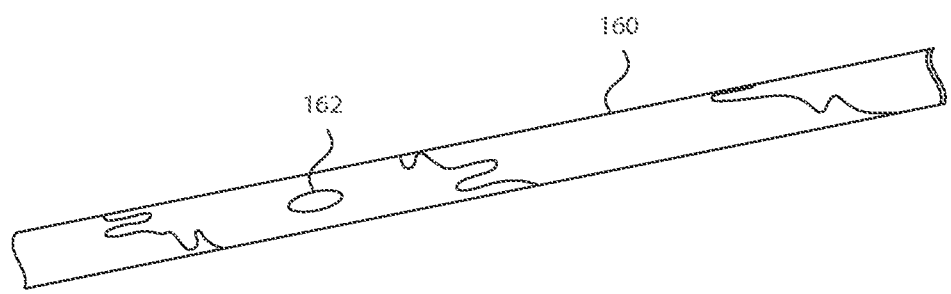
Figure 12:
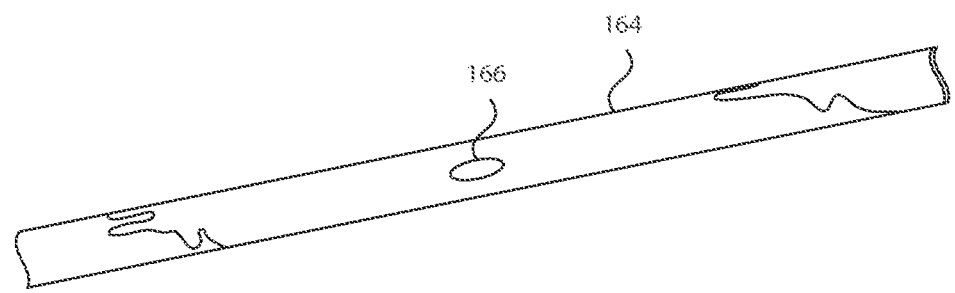

FIGS. 10-12 are perspective views of shaft segments having guide wire exit openings with different positions relative to cuts. For example, with reference to FIGS. 5 and 10, in some embodiments a shaft segment 156 having the first and second cut shapes 128, 130 has a guide wire exit opening 158 in place of a third peak 138 of one of the second cut shapes 130. In other embodiments, the guide wire exit opening 158 can be in place of the first peak 132, the second peak 134, the fourth peak 140, or a combination thereof including or not including the third peak 138. As another example, with reference to FIGS. 5 and 11, a shaft segment 160 having the first and second cut shapes 128, 130 can have a guide wire exit opening 162 between (e.g., about evenly between) adjacent turns of a helical path along which the first and second cut shapes 128, 130 are distributed. As yet another example, with reference to FIGS. 5, 6 and 12, a shaft segment 164 having the first and second cut shapes 128, 130 and the uncut region 146 (e.g., as described above with reference to FIG. 6) can have a guide wire exit opening 166 at the uncut region 146. In other examples, the guide wire exit openings may have other suitable positions relative to the cuts. Furthermore, although the guide wire exit openings 158, 162, 166 are illustrated in FIGS. 10-12 as generally oval with their longitudinal axes aligned with longitudinal axes of the corresponding shaft segments 156, 160, 164, the guide wire exit openings 158, 162, 166 can have other suitable shapes and/or orientations.

Instead of or in addition to a cut tube, neuromodulation catheters configured in accordance with at least some embodiments of the present technology can include one or more elongate members (e.g., filaments, wires, ribbons, or other suitable structures) helically wound into one or more tubular shapes. Similar to the axial density of turns, shapes, or other suitable features of a cut along a longitudinal axis of a shaft (e.g., as discussed above with reference to FIG. 3), the axial density of windings of a helically wound elongate member along a longitudinal axis of a shaft can be selected to change the flexibility of the shaft. For example, an axial density of windings along a longitudinal axis of a shaft can be selected to facilitate intravascular delivery of a neuromodulation element to a treatment location within or otherwise proximate to a renal artery of a human patient via a transradial or other suitable approach. In some embodiments, an axial density of windings along a longitudinal axis of a shaft varies along the length of the shaft (e.g., to tailor the shaft to the tortuosity or other geometry of different portions of a transradial or other suitable approach). In other embodiments, the axial density of windings along a longitudinal axis of a shaft can be consistent along the length of the shaft (e.g., to increase the overall flexibility of the shaft).

Figure 13:
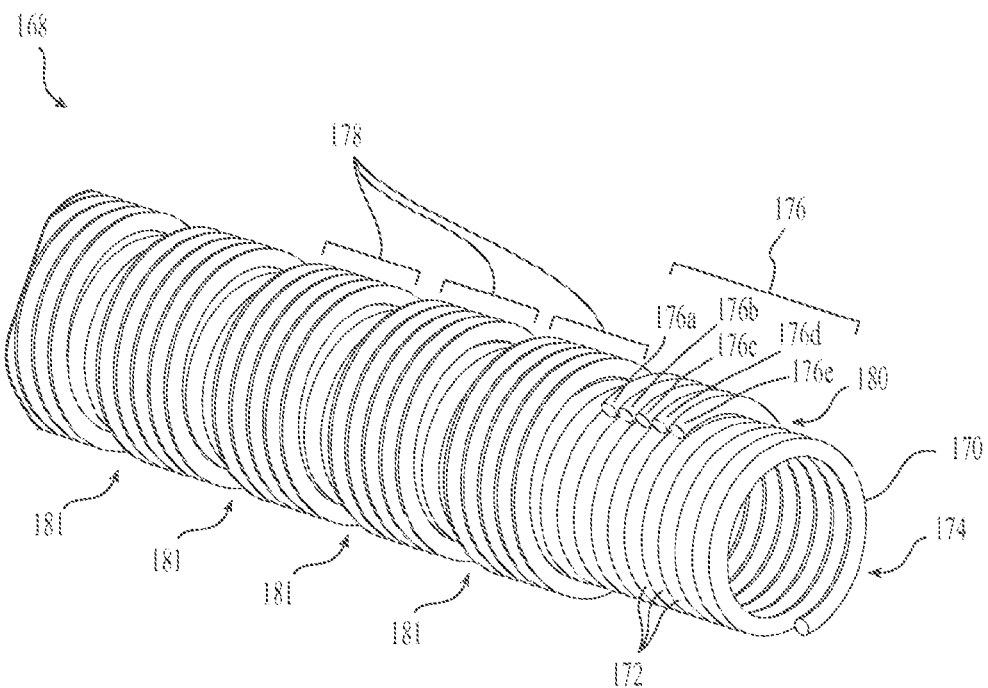
FIGS. 13 and 14 are perspective views of shaft segments including helically wound elongate members configured in accordance with embodiments of the present technology.
Figure 14:
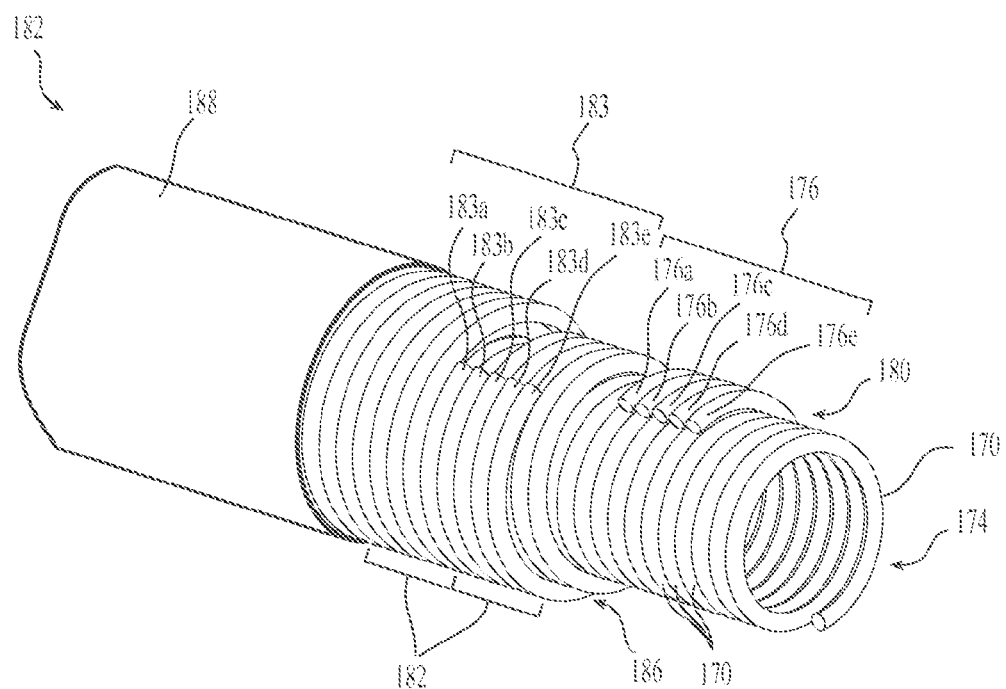

FIGS. 13 and 14 are perspective views of shaft segments including helically wound elongate members configured in accordance with embodiments of the present technology. With reference to FIG. 13, a shaft 168 can include a first helically wound elongate member 170 having a series of first windings 172 at least partially forming a first tubular structure 174. The shaft 168 can further include a second helically wound elongate member 176 having a series of second windings 178 at least partially forming a second tubular structure 180. The first tubular structure 174 can be disposed within the second tubular structure 180, and the first and second tubular structures 174, 180 can be concentric.

In some embodiments, at least one of the first and second helically wound elongate members 170, 176 is multifilar. For example, in the embodiment shown in FIG. 13, the second helically wound elongate member 176 is multifilar with five parallel filaments (individually identified in FIG. 13 as 176a-e), and the first helically wound elongate member 170 is monofilar. In other embodiments, the second helically wound elongate member 176 can be monofilar and the first helically wound elongate member 170 can be multifilar. In still other embodiments, both the first and second helically wound elongate members 170, 176 can be monofilar or multifilar. Furthermore, in some embodiments, the first windings 172, the second windings 178, or both are "openly wound" or spaced apart along a longitudinal axis of the shaft 168. For example, in the embodiment shown in FIG. 13, the second windings 178 are shown spaced apart along the longitudinal axis of the shaft 168 with gaps 181 between adjacent second windings 178, and the first windings 172 are shown not spaced apart along the longitudinal axis of the shaft 168. In other embodiments, the second windings 178 can be not spaced apart along the longitudinal axis of the shaft 168 and the first windings 172 can be spaced apart along the longitudinal axis of the shaft 168. In still other embodiments, both the first and second windings 172, 178 can be spaced apart or not spaced apart along the longitudinal axis of the shaft 168.

With reference to FIG. 14, a shaft 182 can include a third helically wound elongate member 183 having a series of third windings 184 at least partially forming a third tubular structure 186. The first and second tubular structures 174, 180 can be disposed within the third tubular structure 186, and the first, second, and third tubular structures 174, 180, 186 can be concentric. In the embodiment shown in FIG. 14, the third helically wound elongate member 183 is multifilar with parallel filaments (individually identified in FIG. 14 as 183a-e). In other embodiments, the third helically wound elongate member 183 can be monofilar. Furthermore, in embodiments having more than one helically wound layer, the layers may be counter-wound, e.g. a right-hand helical layer may surround a left-hand helical layer. The shaft 182 can further include biocompatible jacket 188 at least partially encasing the first, second, and third tubular structures 174, 180, 186. The biocompatible jacket 188, for example, can be at least partially made of a smooth polymer or other suitable material well suited for sliding contact with an inner wall of a body lumen.

Figure 15:
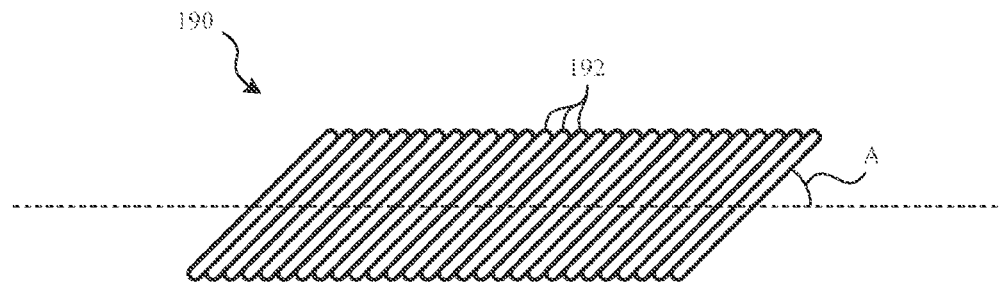
FIGS. 15 and 16 are side profile views of helically wound elongate members having windings with different average helix angles configured in accordance with embodiments of the present technology.
Figure 16:
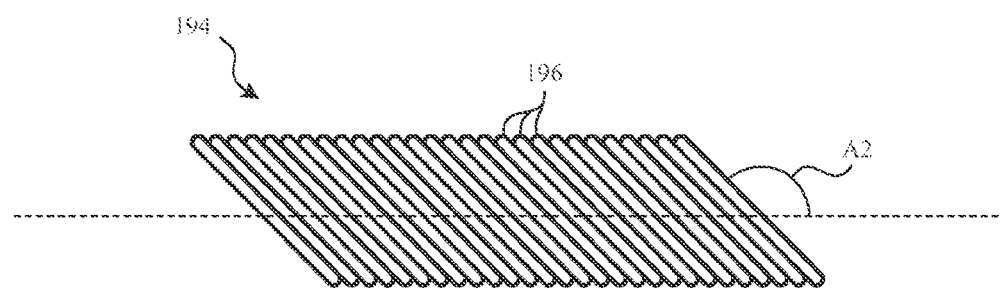

FIG. 15 is a side profile view of a helically wound elongate member 190 having a series of windings 192 with an average helix angle A1. FIG. 16 is a side profile view of a helically wound elongate member 194 having a series of windings 196 with an average helix angle A2. With reference to FIGS. 14-16 together, the first windings 172, the second windings 178, the third windings 184, or a subset thereof, can have different average helix angles. For example, a first average helix angle of the first windings 172 can be different than a second average helix angle of the second windings 178 by an angle within a range from about 10 degrees to about 140 degrees (e.g., a range from about 30 degrees to about 120 degrees, or another suitable range). Similarly, the first average helix angle of the first windings 172 can be different than a third average helix angle of the third windings 184 by an angle within a range from about 10 degrees to about 140 degrees (e.g., a range from about 30 degrees to about 120 degrees, or another suitable range) and the second average helix angle of the second windings 178 can be between (e.g., about midway between) the first and third average helix angles of the first and third windings 172, 184, respectively.

Figure 17:
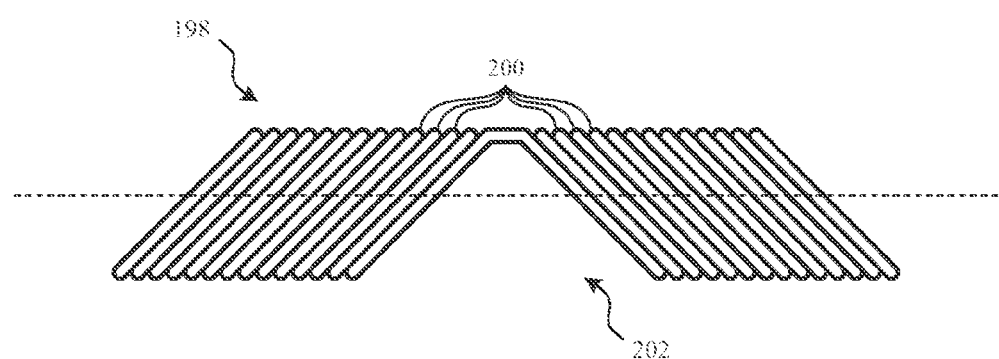
FIG. 17 is a side profile view of a helically wound elongate member having windings with different average helix angles on either side of a transition region configured in accordance with an embodiment of the present technology.

FIG. 17 is a side profile view of a helically wound elongate member 198 having a series of windings 200 with different average helix angles and opposite chirality on either side of a transition region 202. Although an abrupt change in average helix angle at the transition region 202 is shown in FIG. 17, the change at the transition region 202 can alternatively be gradual or incremental. With reference to FIGS. 14, 15 and 17 together, in some embodiments the first windings 172, the second windings 178, and/or the third windings 184 include one or more transition regions 202. In other embodiments, the first windings 172, the second windings 178, and the third windings 184 can have consistent helix angles along the length of the shaft 168. Including one or more transition regions 202 can be useful, for example, to allow a difference between average helix angles of windings within concentric tubular structures to vary (e.g., to change at least once) along the length of the shaft 168. For example, this difference can decrease (e.g., abruptly, gradually, or incrementally) distally along the length of the shaft 168. It is expected that increasing a difference between average helix angles of windings within concentric tubular structures may reduce flexibility and increase axial and torsional stiffness of a shaft, and that decreasing a difference between average helix angles of windings within concentric tubular structures may increase flexibility and decrease axial and torsional stiffness of a shaft. Accordingly, the positions of the transition regions 202 can be selected to change the flexibility of the shaft relative to the axial and torsional stiffness of the shaft along the length of a shaft (e.g., to facilitate intravascular delivery of a neuromodulation element to a treatment location within or otherwise proximate to a renal artery of a human patient via a transradial or other suitable approach).

Instead of or in addition to a cut tube and/or a helically wound elongate member, neuromodulation catheters configured in accordance with at least some embodiments of the present technology can include shafts having one or more segments with different shape memory properties. With reference to FIG. 3, for example, the first segment 127a can be made at least partially of a first shape-memory alloy, the second segment 127b can be made at least partially of a second shape-memory alloy, and the third segment 127c can be made at least partially of a third shape-memory alloy. The first, second, and third shape-memory alloys can be different or the same. In some embodiments, the first, second, and third shape-memory alloys are nitinol. In other embodiments, the first, second, and third shape-memory alloys can be other suitable materials. The first, second, and third shape-memory alloys can have first, second, and third shape-memory transformation temperature ranges, respectively. For example, when the first, second, and third shape-memory alloys are nitinol, the first, second, and third shape-memory transformation temperature ranges can include Af temperatures.

The second shape-memory transformation temperature range and/or an Af temperature of the second shape-memory transformation temperature range can be lower than the first shape-memory transformation temperature range and/or an Af temperature of the first shape-memory transformation temperature range. For example, the first shape-memory transformation temperature range can include an Af temperature greater than body temperature and the second shape-memory transformation temperature range includes an Af temperature less than body temperature. A shape-memory transformation temperature range and/or an Af temperature of a shape-memory transformation temperature range of the shaft 108 can increase (e.g., abruptly, gradually, or incrementally) along the third segment 127c from the second segment 127b toward the first segment 127a. In some embodiments, to vary the shape-memory transformation temperature ranges and/or Af temperatures along the length of the shaft 108, the first, second, and third segments 127a-c are formed separately and then joined. In other embodiments, the shape-memory transformation temperature ranges and/or the Af temperatures along the length of the shaft 108 can be achieved by processing the first, second, and third segments 127a-c differently while they are joined. For example, one of the first, second, and third segments 127a-c can be subjected to a heat treatment to change its shape-memory transformation temperature range and/or Af temperature while the others of the first, second, and third segments 127a-c are thermally insulated.

It is expected that greater shape-memory transformation temperature ranges and/or Af temperatures of shape-memory transformation temperature ranges may increase flexibility and decrease axial and torsional stiffness of a shaft (e.g., by causing nitinol to tend to assume a austenite phase at body temperature), and that lower shape-memory transformation temperature ranges and/or Af temperatures of shape-memory transformation temperature ranges may decrease flexibility and increase axial and torsional stiffness of a shaft (e.g., by causing nitinol to tend to assume a martensite phase at body temperature). Accordingly, the positions of segments of a shaft having different shape-memory transformation temperature ranges and/or Af temperatures of shape-memory transformation temperature ranges can be selected to change the flexibility of the shaft relative to the axial and torsional stiffness of the shaft along the length of a shaft (e.g., to facilitate intravascular delivery of a neuromodulation element to a treatment location within or otherwise proximate to a renal artery of a human patient via a transradial or other suitable approach).

Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment location in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

Returning to FIG. 1, in another embodiment the system 100 may comprise a stent delivery system. In this embodiment, stent delivery catheter 102 includes stent delivery element 112. In one embodiment, stent delivery element 112 includes a dilatation balloon with a balloon expandable stent disposed thereon. The stent delivery catheter 102 also includes handle 110 operably connected to shaft 108 via proximal end portion 108a. The shaft 108 can be configured to locate the stent delivery element 112 intravascularly at a treatment location within or otherwise proximate to a body lumen (e.g., coronary artery). The handle 110 is configured to aid in the delivery and deployment of the stent (not shown) to the treatment location. The stent delivery system 100 does not include the console 104 or cable 106.

The stent of stent delivery element 112 may be any balloon expandable stent as known to one of ordinary skill in the art. In one embodiment, for example, the stent is formed from a single wire forming a continuous sinusoid. The stent may include a coating disposed on the surface of the stent. The coating may include a polymer and/or a therapeutic agent. In one embodiment, the coating includes a Biolinx™ polymer blended with a limus drug. In another embodiment, the stent is a drug filled stent having a lumen filled with a therapeutic agent. In still another embodiment, element 112 does not include a stent disposed on the dilatation balloon.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A neuromodulation catheter, comprising:
an elongate shaft including
a tubular wall,
a first hypotube segment concentrically disposed within the tubular wall, the first hypotube segment being made at least partially of a first shape-memory alloy having a first shape-memory transformation temperature range, and
a second hypotube segment concentrically disposed within the tubular wall proximal to the first hypotube segment along a longitudinal axis of the shaft, the second hypotube segment being made at least partially of a second shape-memory alloy having a second shape-memory transformation temperature range lower than the first shape-memory transformation temperature range; and
a neuromodulation element operably connected to the shaft via a distal end portion of the shaft.

2. The neuromodulation catheter of claim 1 wherein:
the elongate shaft includes a third hypotube segment concentrically disposed within the tubular wall between the first and second hypotube segments along the longitudinal axis, the third hypotube segment being made at least partially of a third shape-memory alloy having a third shape-memory transformation temperature range;
the first, second, and third shape-memory alloys are the same; and
the third shape-memory transformation temperature range gradually increases along the third segment from the second segment toward the first segment.

3. The neuromodulation catheter of claim 2 wherein the first, second, and third shape-memory alloys are nitinol.

4. A neuromodulation catheter, comprising:
an elongate shaft including
a first segment made at least partially of nitinol having a first shape-memory transformation temperature range, and
a second segment made at least partially of nitinol having a second shape-memory transformation temperature range lower than the first shape-memory transformation temperature range, the second segment being proximal to the first segment along a longitudinal axis of the shaft; and
a neuromodulation element operably connected to the shaft via a distal end portion of the shaft,
wherein
the first shape-memory transformation temperature range includes an Af temperature greater than body temperature; and
the second shape-memory transformation temperature range includes an Af temperature less than body temperature.

5. The neuromodulation catheter of claim 1 wherein the neuromodulation element comprises one or more energy delivery elements.

6. The neuromodulation catheter of claim 1 wherein the neuromodulation catheter is configured for electrode-based treatment.

7. The neuromodulation catheter of claim 1 wherein the neuromodulation catheter is configured for heat-element-based treatment.

8. The neuromodulation catheter of claim 1 wherein the neuromodulation catheter is configured for transducer-based treatment.

9. The neuromodulation catheter of claim 1 wherein the neuromodulation catheter is configured for chemical-based treatment.

10. The neuromodulation catheter of claim 9 wherein the neuromodulation catheter is configured for drug infusion.

11. The neuromodulation catheter of claim 9, further comprising a therapeutic element including a plurality of needles.

12. The neuromodulation catheter of claim 1 wherein the neuromodulation catheter is configured for intravascular delivery via a transradial approach.

13. The neuromodulation catheter of claim 1 wherein the neuromodulation catheter is configured for intravascular delivery to a renal artery of a human patient.

* * * * *